(12) United States Patent
Ouchi

(10) Patent No.: US 7,858,940 B2
(45) Date of Patent: Dec. 28, 2010

(54) INFORMATION ACQUISITION APPARATUS AND INFORMATION AQUISITION METHOD USING TERAHERTZ WAVE FOR ACQUIRING INFORMATION ON OBJECT

(75) Inventor: Toshihiko Ouchi, Sagamihara (JP)

(73) Assignee: Canon Kabushiki Kaisha, Tokyo (JP)

( * ) Notice: Subject to any disclaimer, the term of this patent is extended or adjusted under 35 U.S.C. 154(b) by 317 days.

(21) Appl. No.: 12/090,446

(22) PCT Filed: Dec. 12, 2007

(86) PCT No.: PCT/JP2007/074353

§ 371 (c)(1),
(2), (4) Date: Apr. 16, 2008

(87) PCT Pub. No.: WO2008/075696

PCT Pub. Date: Jun. 26, 2008

(65) Prior Publication Data

US 2010/0148069 A1 Jun. 17, 2010

(30) Foreign Application Priority Data

Dec. 18, 2006 (JP) ............................. 2006-339295

(51) Int. Cl.
*G01N 21/00* (2006.01)
(52) U.S. Cl. .................................................. 250/341.1
(58) Field of Classification Search ............... 250/341.1
See application file for complete search history.

(56) References Cited

U.S. PATENT DOCUMENTS 6,239,866 B1 * 5/2001 Bromage et al. ........... 356/5.01

(Continued)

FOREIGN PATENT DOCUMENTS

GB 2 397 207 A1 7/2004

(Continued)

OTHER PUBLICATIONS

Int'l Search Report mailed Mar. 28, 2008, for International Application No. PCT/JP2007074353, not a publication.

(Continued)

*Primary Examiner*—Constantine Hannaher
(74) *Attorney, Agent, or Firm*—Fitzpatrick, Cella, Harper & Scinto

(57) ABSTRACT

An information acquisition apparatus includes a pulse generator 9, a detector 10, a first delay unit 15, a second delay unit 16 and a computation unit. The pulse generator 9 is excited by a first laser beam to generate a terahertz wave in the form of a pulse. The detector 10 is excited by a second laser beam coherent to the first laser beam to detect the terahertz wave from object 2 that is irradiated with the pulse of the terahertz wave. The first delay unit 15 changes the delay time in such a way that the detector 10 can detect the pulse signal of the terahertz wave from the object 2. The second delay unit 16 changes the delay time by not greater than the temporal width of the pulse signal detected by the detector 10. The computation unit computationally determines the information on the temporal position of the peak of the pulse signal of the terahertz wave from the object 2 according to the information of the signal detected by the detector 10 when the delay time is changed by the second delay unit within the delay time of the first delay unit.

10 Claims, 6 Drawing Sheets

U.S. PATENT DOCUMENTS

| | | | |
|---|---|---|---|
| 2002/0067480 A1* | 6/2002 | Takahashi | 356/317 |
| 2006/0217612 A1 | 9/2006 | Ouchi | 600/407 |
| 2006/0235621 A1 | 10/2006 | Cole et al. | |
| 2006/0278830 A1* | 12/2006 | Nishizawa et al. | 250/341.1 |
| 2007/0279136 A1 | 12/2007 | Koyama et al. | 331/107 |
| 2008/0116374 A1 | 5/2008 | Ouchi et al. | 250/306 |
| 2008/0137068 A1 | 6/2008 | Ouchi et al. | 356/51 |

FOREIGN PATENT DOCUMENTS

| | | |
|---|---|---|
| JP | 11-108845 A | 4/1999 |
| JP | 2006-516722 | 7/2006 |
| WO | 03/042670 A1 | 5/2003 |
| WO | 2004/063726 A1 | 7/2004 |

OTHER PUBLICATIONS

Written Opinion of the International Searching Authority mailed Mar. 28, 2008, for International Application No. PCT/JP2007/074353, not a publication.

* cited by examiner

TIME DELAY

INFORMATION ACQUISITION APPARATUS AND INFORMATION AQUISITION METHOD USING TERAHERTZ WAVE FOR ACQUIRING INFORMATION ON OBJECT

This Application is a National Stage filing under 35 U.S.C. §371 of International Application No. PCT/JP2007/074353, filed Dec. 12, 2007.

TECHNICAL FIELD

The present invention relates to an information acquisition apparatus such as an image acquisition apparatus for acquiring information on the properties and the shape of an object (target) by means of an electromagnetic wave and also to an information acquisition method such as an image acquisition method. More particularly, the present invention relates to an information acquisition apparatus such as an image acquisition apparatus for acquiring information on a target by means of an electromagnetic wave having a frequency within the frequency range between 30 GHz and 30 THz (which is referred to as a terahertz wave hereinafter) and also to an information acquisition method such as an image acquisition method using a terahertz wave.

BACKGROUND ART

Non-destructive sensing techniques using terahertz waves have been developed in recent years. They include imaging techniques for safely seeing through objects to examine them instead of X-rays. Such techniques can typically provide applications of electromagnetic waves of the above cited frequency range. Additionally, spectrometric techniques for examining physical properties of substances such as bond conditions in the inside of the substance by determining the absorption spectrum and the complex permittivity of the inside of the substance, analysis techniques for analyzing bio-molecules in the inside of substances and techniques for evaluating the concentration and the mobility of carriers in the inside of substances.

Attempts to check prohibited drugs and dangerous matters hidden in pieces of baggage and in the cloths and the bodies of passengers in airports and customs offices by means of see-through examination apparatus using a terahertz wave have been under way. Examining human bodies by irradiating them with X-rays gives rise to the problem of exposure to radiation and therefore techniques using terahertz waves are believed to be effective. Besides, non-destructive quality examinations are important on production lines in manufacturing plants. Therefore, applications of such techniques to internal examinations of ICs, detection of foreign objects in powdery materials and also detection of defects in molded plastic products are being discussed.

It is important to acquire tomographic images in such applications. Therefore, there has been proposed a technique of irradiating an object of examination with a terahertz wave pulse and analyzing the plurality of pulses produced by reflection in terms of delay time and pulse form to acquire tomographic images (see Patent Document 1: Japanese Patent Application Laid-Open No. 11-108845). The above-cited patent document describes an example of observation of the inside of a flexible disk. There has also been proposed a technique of using a reflected or transmitted wave of a terahertz wave pulse, performing a Fourier transform of the time domain waveform of the pulse, to observe the frequency spectrum in order to display how chemical samples are distributed in the depth direction in the inside of an object, which may be a medicine in most cases (Patent Document 2: Japanese Patent Application Laid-Open No. 2006-516722).

As a suitable technique for generating a terahertz wave, there is a known method of irradiating a laser beam emitted from a femtosecond laser onto a photoconductive switching device prepared by using a photoconductive film formed on a substrate and provided with an antenna that also operates as an electrode is known (see Patent Document 1). While LT-GaAs grown on a substrate at low temperature is popularly employed as photoconductive film, InGaAs, InAs or GaSb may alternatively be used.

DISCLOSURE OF THE INVENTION

However, the proposed technique of using ordinary THz time domain spectroscopy (THz-TDS) as described in Patent Document 2 does not describe the resolution of the object of examination in the depth direction nor any means for improving the resolution. While the patent document shows images at the depths of 0.3 mm, 0.6 mm and 1.2 mm in Examples (see FIG. 12 of Patent Document 2), a high resolution is required in the depth direction in order to actually acquire a tomographic image.

More specifically, the above cited proposed technique is not equipped with a system for coping with different pulses coming from two or more than two reflection points that are located close to each other by processing signals and separating them. Therefore, intensity fluctuations of pulses and jitters of pulse positions operate as noises. Then, under their influences, only pulses that show temporal gaps not smaller than the temporal widths of the pulses can be separated and only a level of resolution in the depth direction of the object of examination that corresponds to the temporal gaps can be achieved.

In view of the above-identified problems, the present invention provides an information acquisition apparatus for acquiring information on an object by means of a terahertz wave, including: a pulse generator adapted to be excited by a first beam of light to generate a terahertz wave pulse; a detector adapted to be excited by a second beam of light coherent to the first beam of light to detect a terahertz wave from the object irradiated with the terahertz wave pulse; a first delay unit for altering the delay time of the second beam of light so as to enable the detector to detect the pulse signal contained in the terahertz wave from the object; a second delay unit for modulating the delay time by an amplitude not greater than the temporal width of the pulse signal detected by the detector; and a computation unit for computationally determining information on the temporal position of the peak of the pulse signal contained in the terahertz wave from the object, using the signal output from the detector when the delay time is modulated by the second delay unit.

Preferably, an information acquisition apparatus as defined above may further include: an image forming unit for forming an image including a tomographic image in the depth direction in the inside of the object, using the information on the temporal position as computationally determined by the computation unit; and a scanning unit for relatively changing the part of the object irradiated by the terahertz wave pulse.

In another aspect of the present invention, there is provided an information acquisition method of acquiring information on an object by means of a terahertz wave, including: a pulse generation step of excitation by a first beam of light to generate a terahertz wave pulse; a detection step of excitation by a second beam of light coherent to the first beam of light to detect a terahertz wave from the object irradiated with the terahertz wave pulse; a first delay step of altering the delay time of the second beam of light so as to enable the detector to detect the pulse signal contained in the terahertz wave from the object in the detection step; a second delay step of modulating the delay time by an amplitude not greater than the temporal width of the pulse signal detected in the detection step; and a computation step of computationally determining information on the temporal position of the peak of the pulse signal contained in the terahertz wave from the object, using the signal detected in the detection step when the delay time is modulated by the second delay unit.

Preferably, an information acquisition method as defined above may further include: an image forming step of forming an image including a tomographic image in the depth direction in the inside of the object, using the information on the temporal position as computationally determined in the computation step; and a scanning step of relatively changing the part of the object irradiated by the terahertz wave pulse. Methods that can be used for acquiring a tomographic image of an object for the purpose of the present invention include those of fixing the position of irradiation of the object to a two-dimensional plane, acquiring information in the depth direction and subsequently scanning the object to change the position of observation and those of specifying a position in the depth direction of the object and repeating an operation of scanning the position of irradiation of the object on a two-dimensional plane, sequentially changing the position in the depth direction.

In still another aspect of the present invention, there is provided an information acquisition apparatus for acquiring information on an object by means of a terahertz wave, including: a pulse generator adapted to be excited by a first beam of light to generate a terahertz wave pulse; a detector adapted to be excited by a second beam of light coherent to the first beam of light to detect a terahertz wave from the object irradiated with the terahertz wave pulse; a first delay unit for altering the delay time of the second beam of light so as to enable the detector to detect the pulse signal contained in the terahertz wave from the object; and a second delay unit for modulating the delay time by an amplitude not greater than the temporal width of the pulse signal output from the detector; information on the temporal position of the peak of the pulse signal contained in the terahertz wave from the object being acquired by using the signal output from the detector when the delay time is modulated by the second delay unit.

Thus, since an information acquisition apparatus according to the present invention includes a second delay unit as described above, it can operate for signal separation in a time not greater than the temporal width of the detected pulse signal and hence correspondingly acquire information on the internal structure of an object with a resolution improved in the depth direction. Thus, information on the internal structure of an object that are not visible from the surface by means of a terahertz wave that is highly capable of penetrating into the object can be acquired with a high resolution.

Particularly, according to the present invention, the resolution in the depth direction can be improved when acquiring a transmitted or reflected tomographic image of an object. Thus, an information acquisition apparatus according to the present invention can operate as a terahertz wave imaging apparatus (image acquisition apparatus) for picking up highly accurate tomographic images in a quality check process on a running production line of industrial products or in an operation of a medial diagnostic apparatus.

Further features of the present invention will become apparent from the following description of exemplary embodiments with reference to the attached drawings.

BEST MODE FOR CARRYING OUT THE INVENTION

As pointed out above, with an information acquisition apparatus and an information acquisition method according to the present invention, excitation by a first beam of light is performed to generate a terahertz wave pulse (a pulse generation step) and excitation by a second beam of light coherent to the first beam of light is performed to detect a terahertz wave from the object irradiated with the terahertz wave pulse (a detection step).

Then, the delay time of the second beam of light relative to the first beam of light is altered so as to enable the detector to detect the pulse signal contained in the terahertz wave from the object (a first delay step) and the delay time is altered by an amplitude not greater than the temporal width of the detected pulse signal (a second delay step). A first delay unit operates for the former alteration and the second delay unit operates for the latter alteration. Thus, information on the temporal position of the peak of the pulse signal contained in the terahertz wave from the object is computationally determined based on the information on the signal detected when the delay time is altered by the second delay unit in the delay time produced by the first delay unit (a computation step).

The computationally determined information on the temporal position can be utilized in various different ways. A reflected pulse is produced when an interface showing a difference of refractive index and/or dielectric constant exists in an object to give rise to a peak of the pulse to be detected. Therefore, it may be sufficient to externally output a signal indicating presence or absence of an interface at a position in the depth direction of the inside of an object that corresponds to the temporal position or a signal indicating the distance separating interfaces that correspond to a displacement of the temporal position. Typically, the computationally determined information is used for forming an image of the inside of the object (an image forming step). Such an image of the inside may be formed only for the site of the object irradiated with a terahertz wave or the irradiated site may be scanned one-dimensionally or two-dimensionally (a scanning step) to form a cross-sectional image or a three-dimensional internal image of the object.

Figure 1:
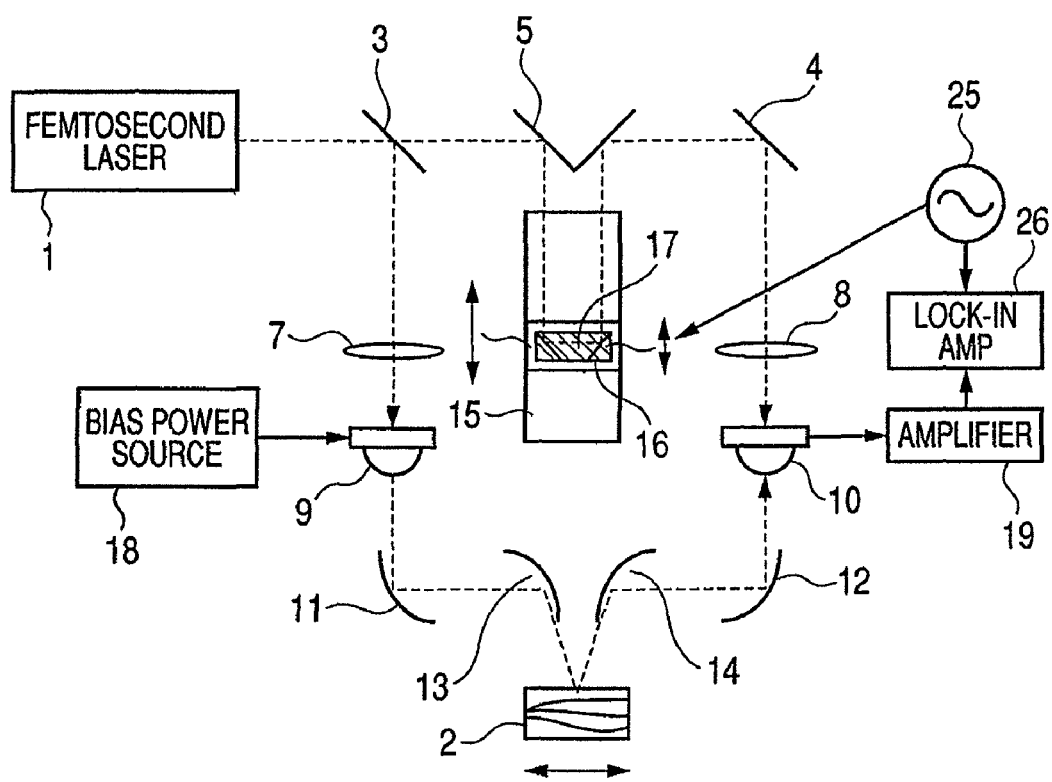
FIG. 1 is a schematic illustration of the image acquisition apparatus and the image acquisition method according to the present invention as used in Example 1.

Now, embodiments of information acquisition apparatus and those of information acquisition method according to the present invention will be described below. FIG. 1 is a schematic illustration of the first embodiment that is an image acquisition apparatus for acquiring a tomographic image of an object by using a reflected wave from the object.

With this embodiment, the laser beam emitted from a femtosecond laser 1 that can generate a light pulse of about 12 fs at wavelength of 800 nm is divided into laser beams that proceed through two respective paths by a beam splitter 3. The first laser beam is converged by a lens 7 and irradiated onto a photoconductive element 9 that is realized by forming an antenna on LT-GaAs (low temperature grown GaAs, which is known to show a very high mobility). As a result, a terahertz wave pulse is generated with a pulse width not greater than 100 fs. The above-described pulse generator is realized by using such a photoconductive element 9.

A photoconductive element formed on an ordinary GaAs substrate shows a disturbed waveform because of the phonon absorption of GaAs. Therefore, it is desirable to prepare an element by transferring only an LT-GaAs film (having a thickness of 2 μm) onto a support substrate that does not show any phonon absorption such as a high resistance Si substrate. However, the element may be formed on an ordinary GaAs substrate or a technique of directly generating from the surface of EC (electro-optical) crystal such as ZnTe or GaSb may be used, although such an arrangement can influence the resolution in the depth direction. A bias DC (direct current) voltage of about 10V is typically applied to the pulse generating side photoconductive element 9 from a power source 18. The generated terahertz wave is increased as the voltage is raised, although saturation may be reached at a voltage depending on the form of the element.

The other laser beam produced by the beam splitter 3, a coherent second laser beam relative to the first laser beam, is irradiated onto another photoconductive element 10 that is the above-described detector by way of a reflector mirror 5 and a delay system and then further by way of a mirror 4 and a lens 8.

The delay system is formed by using stages 15, 16 and a retro-reflector 17 mounted on the stage 16. Thus, the second laser beam is used as gate signal for detecting a terahertz wave. The stage 15 operates as the first delay unit, while the stage 16 operates as the second delay unit. The stages 15, 16 are telescopically and integrally combined to adjust the delay time on the path of one of the laser beams (the second laser beam).

The terahertz wave generated by the photoconductive element 9 is irradiated on the object 2 by way of paraboloidal mirrors 11, 13. The terahertz wave reflected from the object 2 is converged onto the photoconductive element 10 that is the detector by way of paraboloidal mirrors 14, 12. Care should be taken for the arrangement of the photoconductive element 10 that operates as detector as in the case of the photoconductive element 9 that operates as generator.

When the object 2 has a cross sectional structure as illustrated in FIG. 1 (the curves in the object 2 indicate interfaces), a reflected pulse is generated due to the difference of dielectric constant that appears at each of the interfaces.

Thus, a plurality of reflected echo pulses gets to the detector/photoconductive element 10. The terahertz wave that is irradiated onto the object 2 is converged to illustrate a beam diameter of not greater than 1 cm on the surface of the object 2 to become able to show a cross-sectional structure of the object 2. Therefore, the relative positions of the beam of the terahertz wave and the object 2 are shifted along the arrows in FIG. 1 in order to acquire an entire image of the object 2. To move the relative positions two-dimensionally, the terahertz wave and the object are shifted in the direction perpendicular to FIG. 1. Then, a three-dimensional image can be acquired by combining therewith the movement in the depth direction. A scanning unit for driving a holding member that holds the object 2 to move along a guide by means of a drive unit such as a motor may typically be used.

Now, the method of gauging the reflected pulse coming from the object 2, for which a tomographic image is to be acquired, will be described below. This method characterizes this embodiment.

As described above, the delay system includes two stages. The stage 15 is the first stage having a long stroke that can scan by not less than 10 mm and is driven to move at a relatively low speed, whereas the stage 16 is the second stage having a stroke not greater than 10 μm that can oscillate at a high rate between about several kHz and about 100 kHz (the frequency being selected as a function of the oscillation amplitude).

The stroke of the first stage 15 may be determined according to the thickness of the object 2 in the depth direction and that of the second stage 16 may be determined according to the required resolution in the depth direction of the object 2. The moving speed of the first stage is determined according to the speed at which a tomographic image is acquired in the depth direction. It is typically sufficient for it to move several millimeters in tens of several seconds to several minutes. On the other hand, the second stage oscillates at a frequency within an range from several kHz to about 10 kHz that is sufficiently greater than the modulation frequency for acquiring a terahertz signal, which is several hundreds Hz to about 1 kHz. Therefore, the moving speed of the second stage is determined to be about the terahertz pulse width, or the speed necessary for it to be moved by about the electromagnetic wave propagation distance that corresponds to about 100 fs at that frequency.

Any of various motors may be used as unit for driving the first stage 15. The motor that can suitably be used for the first stage 15 may be an ultrasonic wave motor (or a surface wave motor) to be used for driving the zoom lens of a camera, an electromagnetic type linear motor or a stepping motor. On the other hand, a piezoelectric actuator or a MEMS (micro electro mechanical systems) device may be used as unit for driving the second stage 16. The moving speed of the second stage 16 may be raised by using not a linear drive system but a rotary drive system. For example, the angle of incidence of the laser beam entering the prism can be changed to change the distance by which the laser beam propagates in the prism by controlling the rotary motion of the prism by means of a prism transmission system. As the angle of incidence of the laser beam entering the prism is changed, the distance by which the laser beam propagates in the prism changes. Then, as a result, the delay time can be changed quickly with a short stroke.

The operation of the first stage 15 is similar to that of ordinary THz time domain spectroscopy. For example, a pulse that corresponds to a delay time of 40 psec by a stroke of 6 mm can be observed. For example, to five pulse signals that are reflected at the interfaces of the layers in the inside of an object 2 subsequent to the first pulse signal reflected at the uppermost surface of the object 2 can be observed up. To detect a temporal waveform, the voltage of the power source 18 is modulated by about 1 kHz to modulate the pulse string of the terahertz wave irradiated onto the object 2 and detect the output of the photoconductive element 10 by means of an amplifier 19 and a lock-in amplifier 26.

Figure 2A:
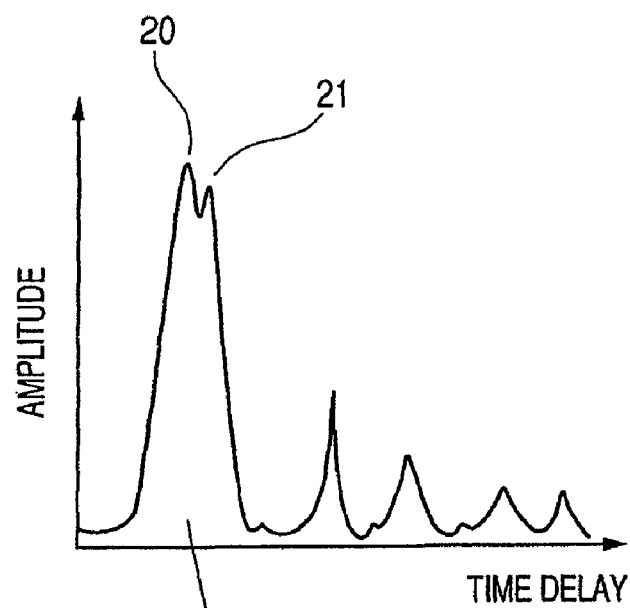
FIGS. 2A, 2B and 2C are schematic illustration of the acquired pulse waveform of a terahertz wave signal.

The oscillator 25 in FIG. 1 is not operated to detect the temporal waveform. When the interfaces in the inside of the object 2 are separated from each other only by small distances, peaks that are close to each other like peaks 20, 21 in FIG. 2A appear to make it difficult to quickly and accurately separate them. When the pulse of the terahertz wave that is irradiated onto the object 2 has a pulse width of 100 fs, the distance in the depth direction of the object 2 by which the pulse peaks can be separated with a time delay of about the pulse width is expressed by the formula shown below.

$$3\times10^8 \text{ (m/s)} \times 100\times10^{-15} \text{ (s)}/2 = 30 \text{ μm}$$

In reality, the resolution falls further due to noises that are attributable to intensity fluctuations of the terahertz wave caused by fluctuations of light from the excitation power source and jitters caused by fluctuations of the pulse position.

In view of this problem, another stage, or the second stage 16, is added onto the first stage 15 and driven to oscillate with an amplitude not greater than the distance that corresponds to the pulse temporal width at a high rate not less than several kHz to modulate the delay time of the second laser beam relative to the first laser beam. The expression of several kHz refers to a range between 0.5 kHz and 5 kHz, although the modulation by the second stage is not limited to several kHz. In other words, the delay time is preferably modulated so as to enable discriminating peaks as will be described in greater detail hereinafter. Then, the detection side for electrically take out only the component of the modulation signal, reduce noises and gauge the peak positions with an enhanced level of sensitivity by way of synchronous detection, using the oscillator 25 and the lock-in amplifier 26 that operate as drive signal source of the second stage 16. Note that, the delay time of the second laser beam can be modulated by an amplitude not greater than the temporal width of the pulse output from the generator.

Figure 3A:
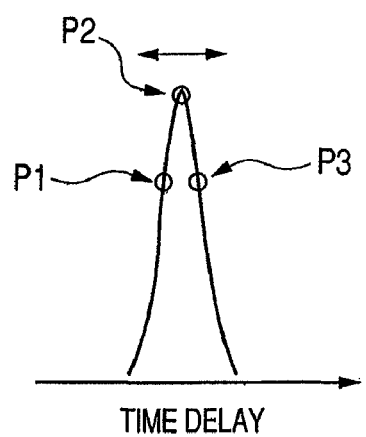
FIGS. 3A, 3B and 3C are schematic illustration of the signal acquisition of the second delay unit in micro oscillations.
Figure 3B:
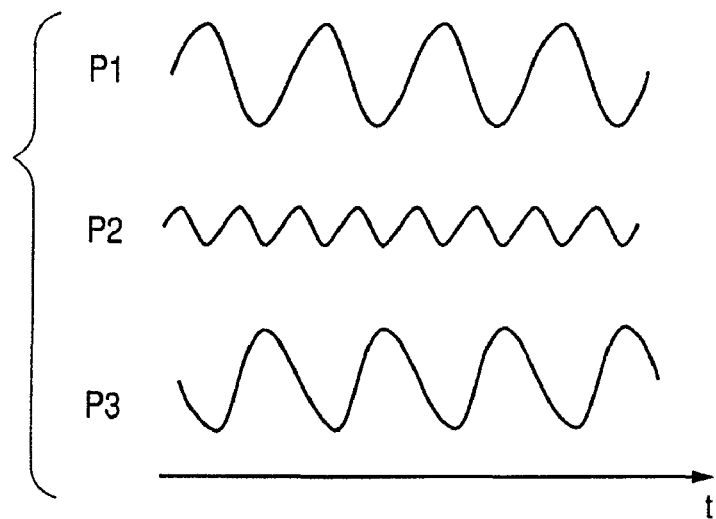

The principle underlying the gauging operation will be described below by referring to FIGS. 3A through 3C. Application of oscillations of a very small amplitude by means of the second stage 16 is equivalent to application of a reciprocation of the delay time relative to the pulse signal of FIG. 3A by a time not greater than the pulse width by means of the second stage 16. The detected signal varies depending on if the center position of the oscillations is located on the positive slope (P1) of the pulse signal, on the peak position (P2) of the pulse signal or on the negative slope (P3) of the pulse signal. FIG. 3B illustrates how the detected signal varies. When, for example, a sinusoidal wave of 10 kHz is used for modulation, an intensity modulating signal of 10 kHz is obtained with a phase that is inverted by 180° between when the center position of oscillations is located at P1 and when the center position of oscillation is located at P2. At this time, the first stage 15 is made either standing still or moving sufficiently slowly relative to the motion of the second stage 16. When, on the other hand, the center position of oscillations is located at point P2, the intensity modulating signal illustrates a frequency of 20 kHz that is twice of 10 kHz.

Figure 3C:
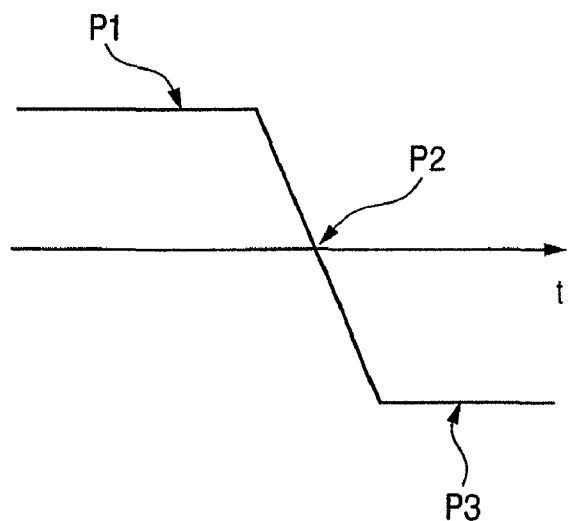

FIG. 3C illustrates the amplitude obtained when the center of oscillations is gradually shifted and the 10 kHz component is taken out by means of a 10 kHz low pass filter (a system different from FIG. 1) or by means of synchronous detection of the lock-in amplifier 26 (the system of FIG. 1). In short, the peak position can be detected as zero cross point where positiveness is switched to negativeness or vice versa. When the motion of the first stage 15 is close to the rate of oscillation of the first stage 15, it is subjected to a Doppler shift. If so, it is only necessary to execute a filter process or a synchronous detection process with the frequency obtained after the shift.

Figure 2B:
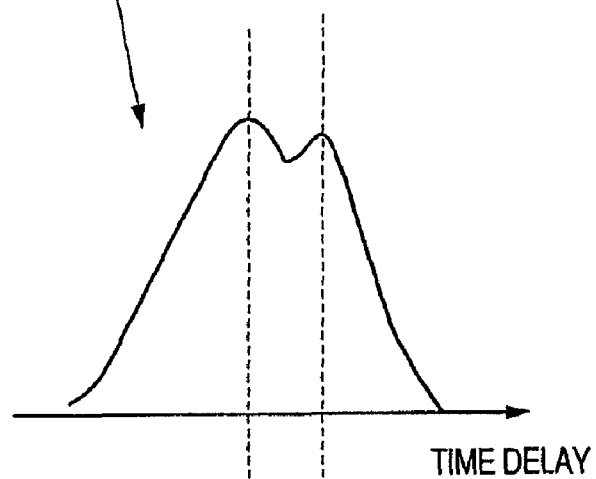
Figure 2C:
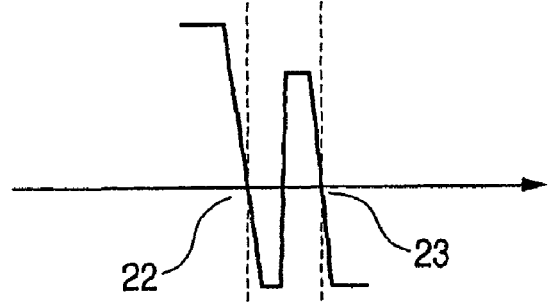

A signal output as illustrated in FIG. 2C is obtained when the above-described operation is applied to peaks 20, 21 that are located close to each other as illustrated in FIG. 2B. Then, that the peak position of the pulse signal is located at points 22 and 23 that are zero cross points where positiveness is switched to negativeness or vice versa can be detected. With this technique, a pulse separation can be performed even when the time difference is not greater than 1/10 of the pulse width. Therefore, when a terahertz wave pulse as described above is used, typically a terahertz tomographic image acquisition apparatus showing a resolution for a depth (in the depth direction) not less than 10 μm of an object 2 can be realized. Then, the output signal of the apparatus as illustrated in FIG. 2C is processed by a computation unit of a control apparatus, which may typically be a personal computer (PC). Information on the temporal positions of the peaks of the pulse signal contained in the terahertz wave coming from the object 2 is computationally determined and a tomographic image of the inside of the object 2 taken in the direction toward the bottom (in the depth direction) is formed by the image forming unit of the control apparatus, which may typically be a PC as pointed out above, and displayed on the display section thereof. The control apparatus, which may typically be a PC, is also equipped with a control unit that stores a program for controlling the operation of each of the components thereof. The above-described configuration is also applied in the examples that will be described hereinafter.

As pointed out above, reflected pulses are produced due to the difference of dielectric constant at each of the interfaces of the layers in the object 2 so that a tomographic image of the object can be obtained by linking the internal positions of the object as viewed in the depth direction that correspond to the temporal positions of the peaks obtained at each scanning point. A more detailed tomographic image can be obtained by acquiring amplitude information, or intensity information, along with the temporal positions of the peaks and executing an imaging process, taking the differences of the absorption coefficients and the refractive indexes of the substances of the layers of the object 2 in the depth direction into consideration. As will be described in greater detail hereinafter, a Fourier transform on the pulse waveform can be performed to acquire frequency information, which is to be taken into consideration.

EXAMPLES

Now, the present invention will be described in greater detail by way of examples.

Example 1

Example 1 according to the present invention corresponds to the embodiment described above by referring to FIG. 1. More specifically, Example 1 is a terahertz wave tomographic image acquisition apparatus having a delay system formed by using two stages 15, 16. The example employs a femtosecond laser 1 showing a pulse width of 12 fs and realized by using a solid such as titanium-sapphire crystal, although the pulse width is by no means limited thereto. The pulse width is to be determined according to the specifications defined for the resolution in the depth direction of the object 2 and hence a pulse width of 100 fs may be selected.

This example employs a stepping motor for driving the first stage 15 and a piezoelectric actuator for driving the second stage 16. As pointed out earlier, the second stage 16 operates for a high-speed modulation shift. For example, a modulation that corresponds to a delay time of 20 fs time is realized by means of a modulation shift of an amplitude (peak to peak) of 3 μm at 10 kHz. Oscillations as described above are applied to the second stage 16, while driving the first stage 15 to scan at a speed of about 10 mm/min, in order to catch the reflected pulse that corresponds to the depth direction of the object 2.

At this time, the relative positions of the object 2 and the irradiating terahertz wave are fixed to acquire information in the depth direction. More specifically, a synchronous detection is realized by means of a modulation signal of 10 kHz for modulating the second stage 16. Thus, a detection signal that shows a zero cross point can be obtained each time there is a peak as described above by referring to FIG. 2C.

In this way, a three-dimensional image of the object 2 as a whole can be acquired by two-dimensionally scanning the object 2 in necessary regions, while a tomographic image taken in the depth direction at each scanning point is acquired. In other words, this example executes the above-described scanning step after executing the computations step at each scanning point in a state where the part of the object 2 irradiated with the pulse of a terahertz wave is fixed.

The above-described method does not involve any operation of obtaining an FFT spectrum from the time waveform unlike the case of an ordinary THz-TDS because a waveform similar to one that can be obtained by differentiating a pulse waveform is obtained. While this method operates without any problem for acquiring a relatively simple tomographic image, a following version can be used for acquiring frequency information in order to know properties of the object 2.

For example, there is a technique for acquiring both a pulse waveform as illustrated in FIG. 2B that can be obtained by means of an ordinary THz-TDS and a peak detection signal as illustrated in FIG. 2C. For this technique, the voltage to be applied to the pulse generating side photoconductive element 9 is modulated by 1 kHz by means of the power source 18. Alternatively, the intensity of the terahertz wave is modulated by means of an optical chopper (not illustrated) of 1 kHz. Then, it is only necessary to acquire signals of two different kinds by band separation. Signals of two different kinds can be obtained by detecting signals, appropriately switching the reference signal on a time division basis by means of a single lock-in amplifier. Of course, two lock-in amplifiers may be used. When a pulse waveform like that of FIG. 2B is obtained, frequency information can be acquired by performing a Fourier transform. Then, the material and the condition of the layer of the part that gives rise to the pulse waveform can be eliminated by comparing the frequency information with the corresponding data stored in a database in advance. The tomographic image to be displayed can be made more meaningful when the obtained information is utilized for the coloring and the gradation of the image.

This example is adapted to use an image acquiring technique of firstly acquiring information on the depth direction at each scanning point and subsequently two-dimensionally scanning the object 2 in order to acquire an image. However, a technique of a one-dimensional or two-dimensional image firstly by scanning the object 2, while rigidly holding the first stage 15 and hence the depth of the position to be observed, and subsequently shifting the position of the first stage 15 stepwise to sequentially accumulate images at different positions in the depth direction. In other words, the latter technique executes the above-described computation step, while executing the scanning step, under the condition where the delay time is fixed to a predetermined value in the first delay step and repeats the above operation.

While a signal acquisition procedure of detecting a reflected pulse is described above, a transmitted pulse may alternatively be detected. When acquiring a transmitted pulse, a pulse reflected for a multiple of times at interfaces of layers of the object 2 showing differences of refractive index is observed by a detector as transmitted pulse. In principle, the same signal processing method can be used for both reflected pulses and transmitted pulses. A larger amount of information can be obtained by analyzing both reflected pulses and transmitted pulses. A more meaningful tomographic image can be displayed by using such a large amount of information. Both the reflected pulse signals and the transmitted pulse signals contain information on the complex permittivity and hence on the refractive indexes and the frequency dispersion spectrums of the substances of the layers of the object 2. Therefore, substances can be identified and, at the same time, the accuracy of acquisition of tomographic images can be improved by computations using the information on thicknesses that can be acquired from reflected pulse signals and information that can be acquired from transmitted pulse signals and a database.

Several possible applications of an image acquisition apparatus and an image acquisition method for acquiring images including tomographic images according to the present invention will be described below. As for industrial products, bubbles, fissures and defects that can exist in the insides of structures of processed work-pieces can be detected and the multilayer structures of such work-pieces including coating layers and protection films can be analyzed. Then, an image acquisition apparatus and an image acquisition method according to the present invention may be used during the manufacturing process or utilized for periodical degradation diagnoses and defect analyses. Examples of objects that can be examined by means of an image acquisition apparatus and an image acquisition method according to the present invention include molded plastic products, various cards, AV apparatus, portable apparatus, office apparatus and components of heavy machines including functional parts and function materials in the inside such as photosensitive members.

As for security checks at air ports, while various techniques can be used to detect objects hidden in the insides of shoes, it is difficult to detect objects fitted to lateral sides of bags and to the insides of cloths and shoes by sewing. However, such objects can be detected by means of an apparatus and a method as described above for this example because they are adapted to reflection imaging and transmission imaging of an object with a high resolution in the depth direction.

Finally, in the field of healthcare and medical services, an apparatus and a method as described above for this example can acquire information that has never been acquirable when extirpating a focal part such as a cancerated part, when observing the inside of an organ by means of an intra-organic observation scope, when observing skin, teeth or blood vessels and when using a mammography. Thus, the present invention can contribute to improvements of diagnostic techniques in the field of medical services.

Example 2

In Example 2 of the present invention, the two stages of an information acquisition apparatus are arranged respectively on two separate paths. In this example, the first stage 40 equipped with a low speed retro-reflector and showing a large stroke is arranged at the detection side and the second stage 41 equipped with a high-speed retro-reflector and showing a small stroke is arranged at the generation side with a mirror 44 interposed between them. Then, the first delay unit and the second delay unit are inserted into respective light paths that are different from each other so as to adjust the delay times of the light paths independently. Note that the blocks of the electric system similar to those of Example 1 are omitted from FIG. 4 and the components same as those of Example 1 are denoted respectively by the same reference symbols.

The influence of mutual interference of the stages such as vibration noises and Doppler shifts can be more reliably eliminated by separating the two stages in the above-described manner.

Figure 4:
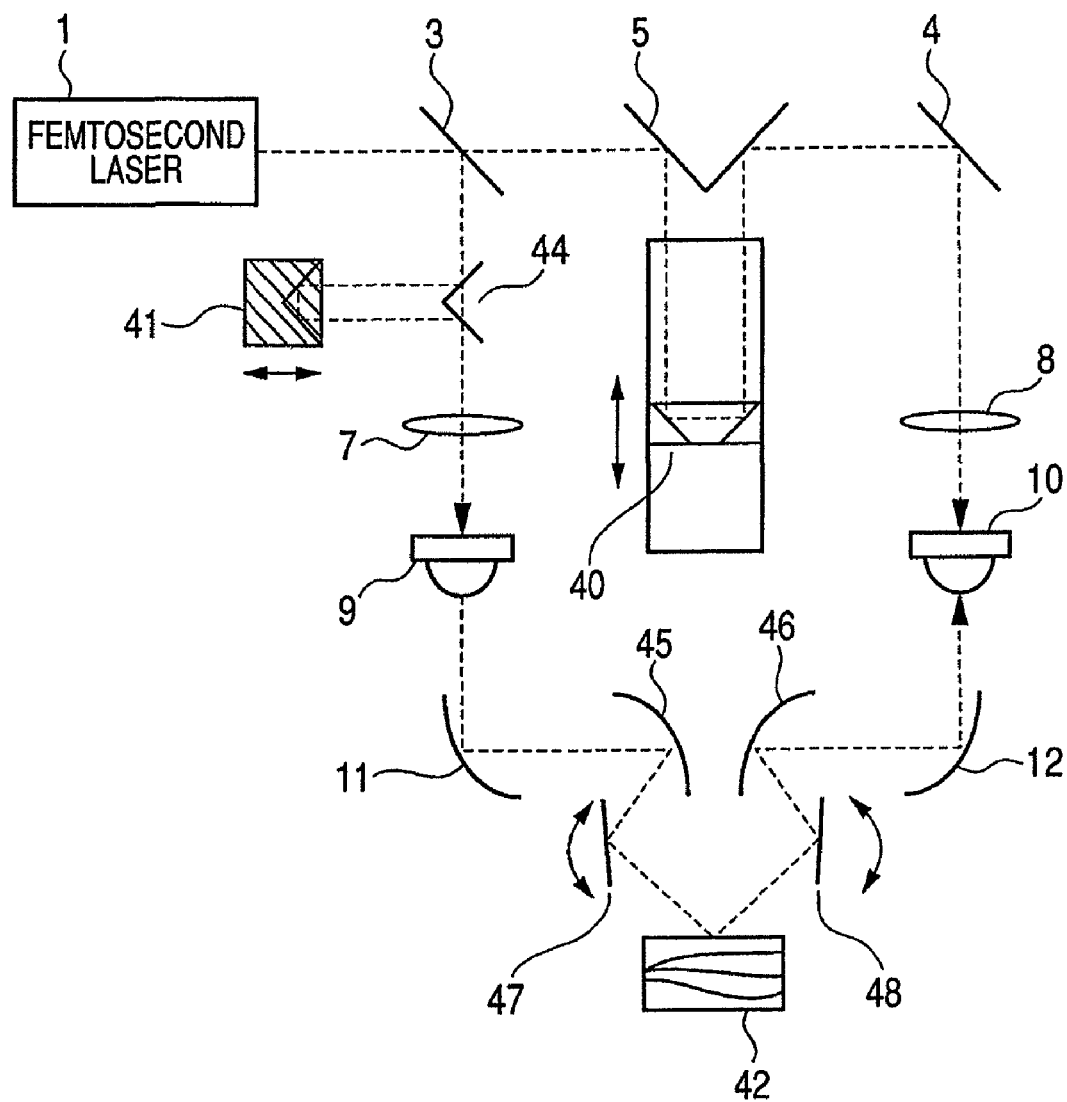
FIG. 4 is a schematic illustration of the image acquisition apparatus and the image acquisition method according to the present invention as used in Example 2.

While Example 1 is adapted to scan the object 2 by moving the latter in order to acquire a tomographic image thereof, alternatively the object 42 may be held stationary and a pair of movable paraboloidal mirrors 45, 46 may be arranged as scanning unit as this example illustrated in FIG. 4. Then, a terahertz wave beam is made to scan the object in order to acquire an image of the whole object by driving the mirrors 47, 48 to move. A terahertz wave beam may alternatively be made to scan the object by using polygon mirrors instead of the galvano-mirrors. Otherwise, this example is same as Example 1.

Example 3

This example of the present invention employs a fiber laser as excitation power source for generating a terahertz wave pulse. Ordinary fiber lasers using an optical fiber that is doped with a rare earth element such as Er as amplification medium so as to oscillate at or near the 1.55 μm band have been developed. Femtosecond lasers of 10 fs or so have been realized as pulse lasers only by using optical fibers.

When an optical fiber is used as excitation power source for generating a terahertz wave, photoconductive elements containing LT-GaAs as in the case of the preceding examples can be used by adding a higher harmonic generating part so as to generate a terahertz wave at a 780 nm band. On the other hand, an LT-InGaAs epitaxial layer formed on an InP substrate or a GaAs substrate may be used to generate a terahertz wave so as to enable the generator directly generate a terahertz wave by means of a fiber laser, using excitation light of a 1.55 μm band or a 1.06 μm band.

Figure 5:
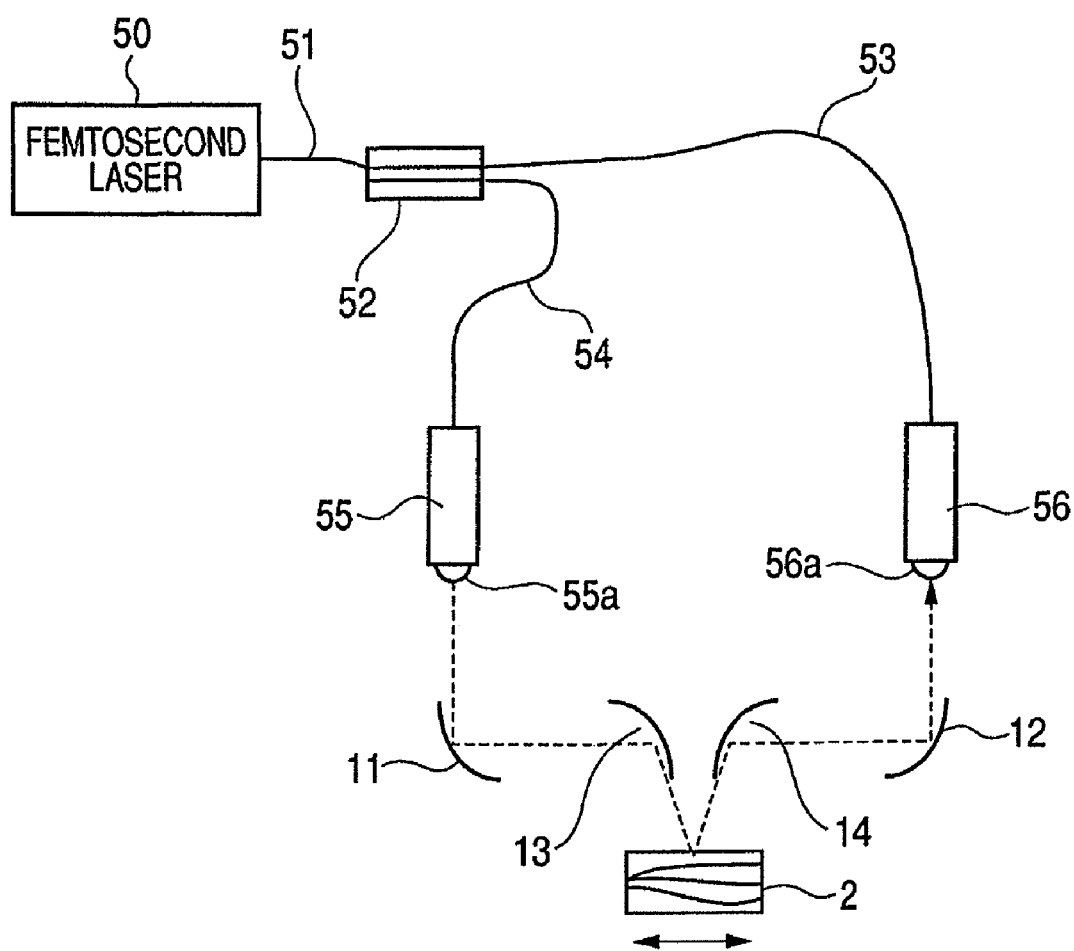
FIG. 5 is a schematic illustration of the image acquisition apparatus and the image acquisition method according to the present invention as used in Example 3.

This example does not require any operation of adjusting the optical axis because the output of the fiber laser 50 is coupled by only optical fibers 51, 53, 54 down to terahertz wave generating section 55 and detection section 56. Additionally, the energy loss can be reduced. With the arrangement of FIG. 5, two optical fibers extend in parallel with each other along a predetermined coupling length in the fiber coupler 52 for branching the laser beam from the fiber laser to produce a first laser beam and a second laser beam and one of the laser beams gets into optical fiber 54, while the other gets into optical fiber 53. Terahertz wave generating section 55 is a module where, for example, a laser beam converging part (which may be moved to somewhere between the optical delay section and the photoconductive element, which will be described below), an optical delay section, a photoconductive element, a terahertz wave generation window and a lens 55a for directivity control are integrally combined. Terahertz wave detecting section 56 is a module where, for example, a lens 56a for directivity control, a terahertz wave generation window, a photoconductive element, an optical delay section and a laser beam converging part (which may be moved to somewhere between the optical delay section and the photoconductive element) are integrally combined. The optical delay sections may be formed by applying a pair of electrodes to an optical fiber where a laser beam passes or an electric crystal in order to adjust the delay time by modulating the voltage applied to it and changing the refractive index of a predetermined part. The magnitude of the voltage and the rate of modulation are respectively made large and low at the first delay unit side, whereas they are respectively made small and high at the second delay unit side. Note again that the blocks of the electric system similar to those of Example 1 are omitted from FIG. 5.

As described above, an optical delay section of a long stroke and an optical delay section of a short stroke are contained respectively and separately in the terahertz wave generating section 55 and the detection section 56. As pointed out above, the optical delay sections can be arranged in a module that is formed only by optical fibers or a module partly connected to optical fibers. Thus, the refractive index of the medium such as the optical fibers is made to change by changing the electric field or the temperature to thereby give rise to a propagation delay. Therefore, when only the above-described delay unit are used, the delay time may become variable if frequency dispersion occurs and hence depending on the frequency component contained in the pulse. There may be occasions where the pulse waveform needs to be trimmed by adjusting the delay time for each frequency typically by means of a chirped fiber grating.

When an image acquisition apparatus is made to include a fiber laser like this example, the apparatus is downsized and less costly if compared with an apparatus including a solid laser and also provides advantages including excellent oscillation stability. Otherwise, this example is same as Example 1.

Example 4

While an image is acquired in the depth direction at each observation point by the preceding examples, the obtained tomographic images can show discontinuous parts because no consideration is give to the transversal distribution in each tomographic image.

This example is adapted to control the first delay unit so as to change the delay time produced by the first delay unit, following the peak position of the reflected pulse, and realize an intra-surface scanning operation for scanning the peak position. In other words, an image can be acquired, putting stress on transversal continuity, by transversally tracing an interface of layers in the inside of the object.

Figure 6:
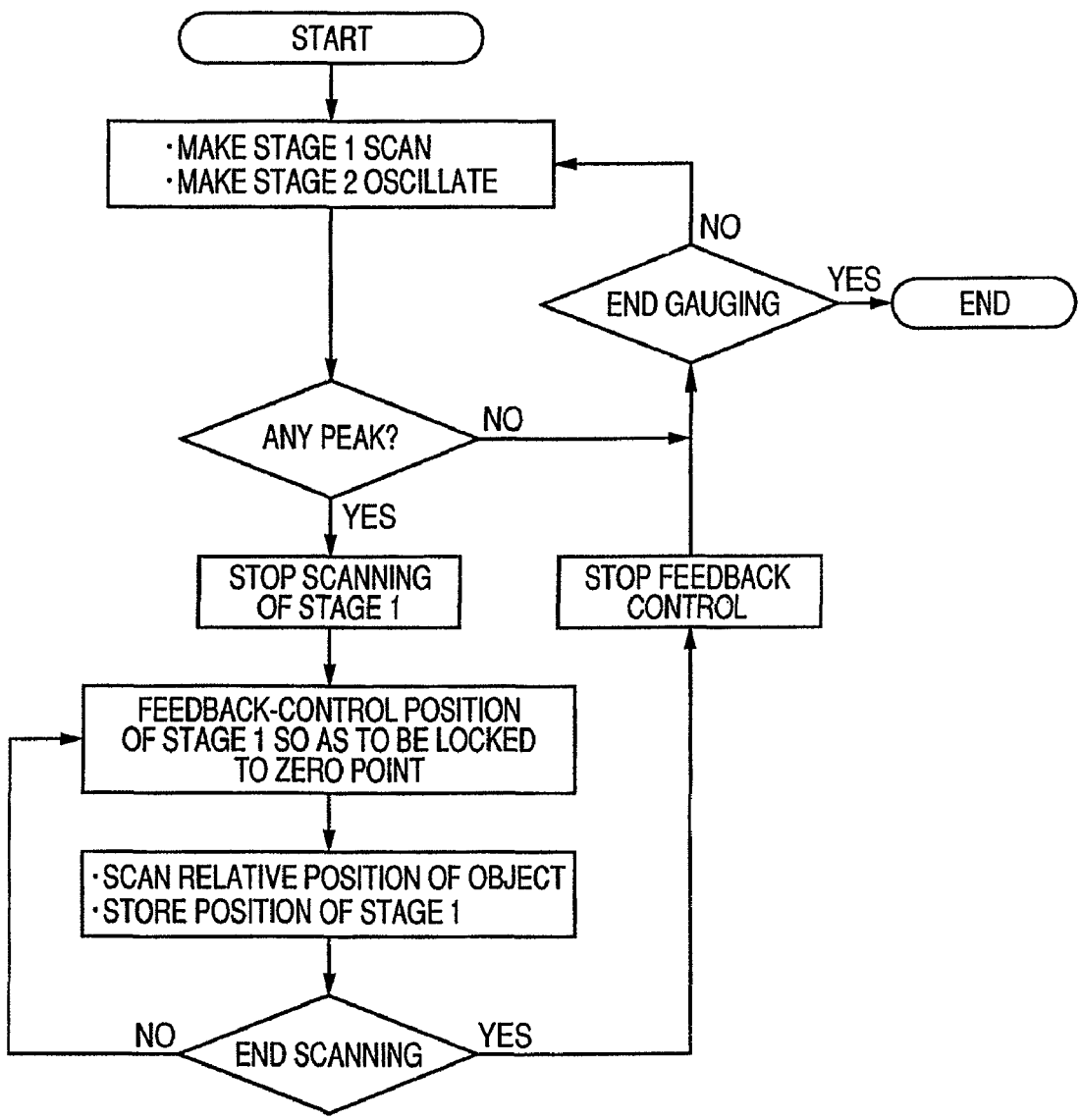
FIG. 6 is a flowchart illustrating the fourth embodiment of image acquisition method according to the present invention.

While the configuration of the apparatus is similar to those of the preceding examples, the system control process of this example differs from those of the preceding examples. This will be described below by referring to the flowchart of FIG. 6.

After starting a gauging operation, the first stage 15 is driven for scanning, while driving the second stage 16 to give rise to micro oscillations, in order to detect a peak. As described earlier, the first stage 15 is driven for scanning until a zero cross point is detected and the existence of a peak is recognized. The scanning operation of the first stage 15 is stopped when a peak is detected and a feedback control operation is conducted for the position of the first stage 15 so that the signal output may be sticking to the zero cross point. Then, the delay position of the first stage 15 that is obtained in response to the feedback control of locking scanning operation to the pulse position, while scanning the relative positions of the object 2 and the terahertz wave beam, is stored in a memory. With this arrangement, the position in the dept direction of the interface of layers in the object 2 that operates as reflection surface can be followed for the gauging operation.

When the operation of two-dimensionally scanning the object 2 ends, the feedback control is terminated and the first stage 15 is driven again for scanning in order to detect the next peak. The above-described operation cycle is repeated until all the interfaces are traced, when the gauging operation is terminated.

Thus, the information acquisition method according to the present invention for acquiring information on an object by means of a terahertz wave proceeds in the following manner for this example. The computations step is executed while the scanning step is being executed in a state where the delay time is made adjustable to or near a predetermined time period in the first delay step. Subsequently, the computation step is executed while the scanning step is being executed in a state where the delay time of the first delay step is made adjustable to or near another predetermined time period. The above operation cycle will repeated thereafter. In a state where the delay time is made adjustable to or near a predetermined time period, the delay time of the first delay step is subjected to feedback control so that the peak of the pulse signal contained in the terahertz wave from the object may be constantly detected while the scanning step is being executed. The delay time will be stored.

With the above-described technique, the distribution of a layer in the transversal directions can be acquired more accurately when compared with the technique of acquiring and synthesizing a tomographic image for each scanning point.

While the present invention has been described with reference to exemplary embodiments, it is to be understood that the invention is not limited to the disclosed exemplary embodiments. The scope of the following claims is to be accorded the broadest interpretation so as to encompass all the modifications and equivalent structures and functions.

This application claims priority from Japanese Patent Application No. 2006-339295, filed on Dec. 18, 2006, which is hereby incorporated by reference herein in its entirety.

The invention claimed is:

1. An information acquisition apparatus for acquiring information on an object by means of a terahertz wave, comprising:
    a pulse generator adapted to be excited by a first beam of light to generate a terahertz wave pulse;
    a detector adapted to be excited by a second beam of light coherent to the first beam of light to detect a reflected or transmitted terahertz wave from the object irradiated with the terahertz wave pulse;
    a first delay unit for altering a delay time of the second beam of light so as to enable the detector to detect a pulse signal contained in the terahertz wave from the object;
    a second delay unit adapted to be driven to oscillate with an amplitude not greater than a temporal width of the pulse signal detected by the detector at a predetermined frequency to modulate the delay time; and
    a computation unit for computationally determining information on a temporal position of a peak of the pulse signal contained in the terahertz wave from the object, using an output signal from the detector when the delay time is modulated by the second delay unit, by taking out a frequency component of the predetermined frequency from the output signal.

2. The information acquisition apparatus according to claim 1, further comprising:
    an image forming unit for forming an image including a tomographic image in the depth direction in the inside of the object, using the information on the temporal position as computationally determined by the computation unit.

3. The information acquisition apparatus according to claim 1 or 2, further comprising:
    a scanning unit for relatively changing the part of the object irradiated by the terahertz wave pulse.

4. An information acquisition method of acquiring information on an object by means of a terahertz wave, comprising:
    a pulse generation step of excitation by a first beam of light to generate a terahertz wave pulse;
    a detection step of excitation by a second beam of light coherent to the first beam of light to detect a terahertz wave from the object irradiated with the terahertz wave pulse;
    a first delay step of altering a delay time of the second beam of light so as to enable the detector to detect a pulse signal contained in the terahertz wave from the object in the detection step;
    a second delay step adapted to be driven to oscillate with an amplitude not greater than a temporal width of the pulse signal detected in the detection step at a predetermined frequency to modulate the delay time; and
    a computation step of computationally determining information on a temporal position of a peak of the pulse signal contained in the terahertz wave from the object, using an output signal from the detector when the delay time is modulated by the second delay unit, by taking out a frequency component of the predetermined frequency from the output signal.

5. The information acquisition method according to claim 4, further comprising:
    an image forming step of forming an image including a tomographic image in the depth direction in the inside of the object, using the information on the temporal position as computationally determined in the computation step.

6. The information acquisition method according to claim 4 or 5, further comprising:
    a scanning step of relatively changing the part of the object irradiated by the terahertz wave pulse.

7. The information acquisition method according to claim 6, wherein
    the computation step is executed in a state where the part of the object that is irradiated by a terahertz wave pulse and subsequently the scanning step is executed.

8. The information acquisition method according to claim 6, wherein
    the computation step is executed, while the scanning step is being executed in a state where the delay time of the first delay step is fixed to a first time period or made adjustable to or near the first time period, and subsequently also the computation step is executed, while the scanning step is being executed in a state where the delay time of the first delay step is fixed to a second time period or made adjustable to or near the second time period.

9. The information acquisition method according to claim 8, wherein
    the delay time of the first delay step is fed back under control so that the peak of the pulse signal contained in the terahertz wave from the object may constantly be detected in the detection step in a state where the delay time of the first delay step is made adjustable to or near the first and second time periods and the delay time is stored in a memory.

10. An information acquisition apparatus for acquiring information on an object by means of a terahertz wave, comprising:
    a pulse generator adapted to be excited by a first beam of light to generate a terahertz wave pulse;

a detector adapted to be excited by a second beam of light coherent to the first beam of light to detect a terahertz wave from the object irradiated with the terahertz wave pulse;

a first delay unit for altering a delay time of the second beam of light so as to enable the detector to detect a pulse signal contained in the terahertz wave from the object; and a second delay unit adapted to be driven to oscillate with an amplitude not greater than a temporal width of the pulse signal output from the detector at a predetermined frequency to modulate the delay time;

information on a temporal position of a peak of the pulse signal contained in the terahertz wave from the object being acquired by using an output signal from the detector when the delay time is modulated by the second delay unit, by taking out a frequency component of the predetermined frequency from the output signal.

* * * * *